United States Patent
Gabel et al.

(10) Patent No.: US 6,852,337 B2
(45) Date of Patent: Feb. 8, 2005

(54) CARVEDILOL-GALENICS

(75) Inventors: Rolf-Dieter Gabel, Schwetzingen (DE); Walter Preis, Neustadt (DE); Alexander Wirl, Heuchelheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 10/278,191

(22) Filed: Oct. 22, 2002

(65) Prior Publication Data

US 2003/0118643 A1 Jun. 26, 2003

Related U.S. Application Data

(63) Continuation of application No. 09/647,639, filed as application No. PCT/EP99/02270 on Jan. 4, 1999.

(30) Foreign Application Priority Data

Apr. 9, 1998 (DE) .......................................... 198 16 036
Jul. 2, 1998 (EP) ............................................. 98112241

(51) Int. Cl.$^7$ ................................................ A61K 9/14
(52) U.S. Cl. ..................................... 424/489; 424/490
(58) Field of Search ................................ 424/489, 490, 424/464

(56) References Cited

U.S. PATENT DOCUMENTS

| | | | | |
|---|---|---|---|---|
| 4,601,895 A | * | 7/1986 | Streuff et al. ................ | 424/479 |
| 5,643,591 A | * | 7/1997 | Mehra et al. ................ | 424/408 |
| 5,948,438 A | * | 9/1999 | Staniforth et al. .......... | 424/464 |
| 6,224,909 B1 | * | 5/2001 | Opitz et al. .................. | 424/489 |

FOREIGN PATENT DOCUMENTS

| | | | |
|---|---|---|---|
| WO | WO 96/13251 | 5/1996 | |
| WO | WO 9810754 A1 | * 3/1998 | ............ A61K/9/22 |

OTHER PUBLICATIONS

Remington: The Science and Practice of Pharmacy, Chapter 91 Powders, 19th Edition, vol. II, 1995, pp. 1598–1614, 1627–1628.*

DAB (Deutsches Arzneibuch) 9 commentary, vol. 1, 9$^{th}$ ed., 1986.

USP (United States Pharmacopoea) 24, p. 2254.

Registration documents for Carvedilol–12.5 mg; Part II: Chemical Pharmaceutical and Biological Documentation, vol. 1 of 2; Part IIC: Control of Starting Materials.

Patent Abstracts of Japan, Japanese Patent Publication (KOKAI) No. 76516/1995, Toyobo Co., Ltd., Mar. 20, 1995.

* cited by examiner

*Primary Examiner*—James M. Spear
(74) *Attorney, Agent, or Firm*—George W. Johnston; Patricia S. Rocha-Tramaloni

(57) ABSTRACT

The invention relates to a process for the preparation of fast-dissolving pharmaceutical preparations from difficultly soluble active substances, wherein an aqueous suspension is made from the active substance and one or more water-soluble adjuvants and then the resulting aqueous suspension is processed, with removal of the water, by methods conventional per se, to form solid pharmaceutical preparations. The invention also relates to fast-dissolving pharmaceutical preparations of active substances having a dissolution rate of at least 70% after 30 minutes, prepared in accordance with the process of the invention.

14 Claims, No Drawings

CARVEDILOL-GALENICS

This is a continuation of U.S. patent application Ser. No. 09/647,639, filed Oct. 2, 2000, which is currently pending which is a 371 of PCT/EP99/02270, filed Jan. 4, 1999.

The invention relates to a process for the preparation of fast-dissolving pharmaceutical preparations from difficultly soluble active substances which tend to agglomerate, with a dissolution rate of at least 70% after 30 minutes, and pharmaceutical preparations made by this process.

In the case of drugs which cannot develop their action in the gastrointestinal zone itself, release from the drug form in the gastrointestinal tract and the subsequent resorption are the necessary condition for a therapeutic effect. Problems arise in this connection with those active substances which, because of their poor solubility or their low dissolution speed, attain so low a concentration in the gastrointestinal tract in the aqueous medium or because of obstructed release from the system of the other adjuvants, that the dissolution of the active substance is the step which determines the rate in connection with the resorption. Because of the low resorption speed as a result, such active substances do not then achieve adequate bioavailability. Problematic drugs of this kind are normally said to be active substances which have a solubility of less than 5 g/l water or the dissolution rate of which from a solid drug form is less than 50% after 30 minutes. The solubility and release rate are determined by standard methods, e.g. in accordance with the paddle method of USP XXII.

Since there are relatively narrow limits to increasing the solubility due to the nature of the active substances (examples are salt formation, derivatisation with solubility-improving groups which do not influence the action or which are split off again in the blood, the production of soluble solvates or other complexes or conversion to high-energy and hence better-soluble crystal forms), the main attention in the past has been devoted to increasing the dissolution speed. Since, according to the known Fick's laws, the speed of dissolution is proportional to the area of the active substance, the concentration gradient of the active substance between the surface of the particles and the solution, and the thickness of the diffusion film adhering to the particles, there are three options for increasing the dissolution speed in the case of diffusion coefficients determined by the active substance and solution medium.

The thickness of the diffusion layer is practically dependent on the movement of the active substance particles in the gastrointestinal tract and hence capable of relatively little influencing. There are relatively narrow limits to increasing the concentration gradients, since the most rapid possible distribution of the active substance particles over the gastrointestinal area available can be obtained only by the addition of disintegrating agents and surfactants. For this reason, the largest possible active substance area is produced. For example, active substances are converted by fine comminuting or rapid precipitation into a microcrystalline or amorphous state, or else a molecular-dispersed, amorphous or microcrystalline distribution of the active substance in the adjuvant is obtained by dissolving in the melt or dissolving a readily soluble adjuvant followed by solidification or evaporation of the solvent.

However, it has been found that the microcrystalline or amorphous active substance particles obtained by comminuting or precipitation tend to recrystallise due to their very high surface energy during processing, particularly under pressure or the addition of solvents and in the case of fairly long storage, so that the surface area and hence the dissolution speed falls off uncontrollably. It has also been found that fine particles tend to combine to form relatively solid agglomerates which even when introduced into a solvent can be separated only with difficulty and therefore behave like a correspondingly larger particle of lower specific surface area. Consequently, such active substances are comminuted together with the soluble adjuvants in excess in order thus to achieve physical separation of the active substance particles by excipient particles. However, even with a considerable excess of adjuvants, recrystallisation or agglomeration of the active substance particles cannot be completely prevented by these steps, so that the dissolution speed of such preparations is not optimal, and particularly not time-independent.

The second possibility of obtaining finely divided active substances is to divide the active substance in a matrix of a hydrophilic readily soluble adjuvant. In this connection, water-soluble polymers have proved particularly suitable, such as polyvinyl pyrrolidone, polyethylene glycol and others. Depending on the properties of the active substance, this can be achieved by dissolving the active substance in a melt of the adjuvant and dispersing this either by spray solidification or by comminuting the solidified melt, whereupon the resultant particles are processed into granulates or tablets, if required after mixing with other adjuvants. If the active substance is not adequately soluble, or if it is damaged by the adjuvant substance melt temperature, the two components can also be dissolved in a suitable solvent from which they are recovered in the form of a substantially homogeneous mixture after removal of the solvent. A disadvantage of this process in particular is that the difficult solubility of the active substance in water means that practically only organic solvents can be used, the processing of which is accompanied by known problems of workplace safety and environmental pollution.

Moreover, because of the solubility conditions, not all active substances can be processed in this way, and the resulting amorphous or molecular-dispersed distributions of the active substance in the adjuvant matrix tend to recrystallise and hence tend to change the dissolution speed of the active substances.

The object of the invention was to develop an efficient and environmentally friendly process for the preparation of fast-dissolving pharmaceutical preparations from difficultly soluble active substances which normally have a dissolution rate of less than 50% after 30 minutes and tend to agglomerate or recrystallise. Another object of the invention was to prepare fast-dissolving pharmaceutical preparations of difficultly soluble active substances such as, for example, carvedilol.

The problem underlying the invention is surprisingly easily solved by the preparation of an aqueous suspension from difficultly soluble active substance and one or more water-soluble adjuvants followed by processing of this aqueous suspension to form solid formulations with removal of the water.

More particularly, the invention relates to a process for the preparation of fast-dissolving pharmaceutical preparations from difficultly soluble active substances having a dissolution rate of at least 70% after 30 minutes, wherein an aqueous suspension is prepared from the active substance and one or more water-soluble adjuvants and then the resulting aqueous suspension is processed, with removal of the water, by conventional processes to form solid pharmaceutical preparations.

According to the invention, difficultly soluble active substances, such as, for example, carvedilol, are mixed with an aqueous solution of one or more suitable adjuvants and then the water is stripped off. It has been found particularly advantageous to use the active substance in a particle diameter of less than 500 μm, preferably a particle diameter of less than 250 μm, particularly preferably with a particle diameter of less than 100 μm. The active substance is mechanically comminuted for the purpose by methods known per se.

In one preferred embodiment, carvedilol or 4-[2-hydroxy-3-[4-(phenoxymethyl)piperidino]-propoxy]-indole are used as active substances.

The term "adjuvants" according to the invention means any readily water-soluble pharmaceutically unobjectionable substances which do not have a negative reaction with the active substance. Thus all conventional binders, fillers, disintegrating agents and/or surfactants (wetting agents, surface-active agents) are used. Mono and disaccharides, for example saccharose, glucose and lactose; oligo and polysaccharides, for example starch; sugar alcohols, for example mannitol and sorbitol; readily water-soluble cellulose derivatives, such as, for example, methylhydroxypropyl cellulose; polyvinylpyrrolidones and polyethylene glycols are preferred. In addition, all other known pharmaceutical adjuvants can be used.

Readily water-soluble adjuvants are preferred since, depending on the solubility of the adjuvant, corresponding quantities of water have to be removed again. To avoid high expenditure in removing the water, the quantity of adjuvant is therefore kept as low as possible.

Thus the active substance/adjuvant ratio in the dry substance in the suspension is in the range from 1:0.01 to 1:500, preferably in the range 1:0.1 to 1:50, particularly preferably 1:0.1 to 1:10, depending on the type and magnitude of the formulation and the quantity of necessary substances and excipients.

If required, surfactants are added to the aqueous suspension of the difficultly soluble active substance, the ratio of active substance to surfactant being in the range of up to 1:1, preferably up to 1:0.3, and up to 1:0.05 in a particularly preferred embodiment.

The surfactants used may be both ionic and non-ionic, for example benzalkonium chloride, polyoxyethylene polyoxypropylene copolymers (e.g. Pluronic F68), alkylsulphates, preferably sodium dodecyl sulphate and stearates, such as polyethylene glycol-400-stearate (Myrj).

According to one embodiment of the invention, a surfactant is dissolved in water and the difficultly soluble active substance is admixed in this solution together with one or more adjuvants.

In addition, a water-insoluble excipient can be additionally admixed in the aqueous suspension of active substance and adjuvants, or else the aqueous suspension is applied to a water-insoluble excipient of this kind. The proportion of water-soluble excipient in relation to the active substance can be up to 50:1. In a preferred variant the difficultly soluble active substance is stirred into an aqueous adjuvant solution together with the water-insoluble excipient and, if required, together with other water-soluble adjuvants.

The water-insoluble excipients are preferably highly dispersed silicon dioxide or aluminium oxide. The proportion of highly dispersed silicon dioxide or aluminium oxide used is up to 20%, based on the solid active substance.

The conversion of the preferably aqueous suspension into solid pharmaceutical preparations following upon the preparation of the preferably aqueous suspension is effected by methods known per se. For example, a preferred variant is spray drying, as a result of which, depending on the dryer size and the type of atomisation, powders or granulates or obtained. These powders or granulates (powders after prior granulation possibly) are processed further into solid drug forms such as, for example, tablets, dragees, capsules, pellets or globules. If required, other conventional adjuvants, for example fillers such as hydrophilic carbohydrates, such as sugar for example, preferably glucose, lactose and saccharose, e.g. sugar alcohols, such as mannitol and sorbitol; for example starch and starch derivatives; binders, such as, for example, gelatin, microcrystalline cellulose, polyvinyl pyrrolidone derivatives and L-HPC; disintegrating agents, for example carboxymethyl cellulose, starch 1500 and sodium carboxyrmethyl starch, ionic and non-ionic surfactants, lubricants, for example talcum or polyethylene glycols; lubricating agents and mould release agents, for example magnesium or calcium stearate, stearic acid, 1-hexadecanol; flow regulators, for example highly dispersed silicon dioxide, and talcum may also be admixed if required.

In other variant, the aqueous suspension is used directly for wet granulation, e.g. in a fluidised bed or in a high speed mixer, possibly with the said conventional adjuvants, and the resulting granulate is dried and further processed in manner known per se. By evaporation of the water the active substance particles are initially coated with a layer of the adjuvants dissolved in the suspension. In addition, these coated particles are combined with the original adjuvants to form larger units. If the suspension volume is high in relation to the original adjuvant volume, wet granulation is advantageously carried out in a number of steps, i.e., intermediate drying steps are interposed during granulation.

In another variant of the invention, the suspension containing the active substance is applied to pellets or globules or used for the preparation of pellets.

In another variant of the process, a solid pharmaceutical preparation is made by spray drying from the active substance suspended in meltable adjuvants, and this suspension can as a variant also contain a highly dispersed excipient, e.g. silicon dioxide.

The process according to the invention has the advantage that there is no need to use organic solvents or high temperatures.

It has been found that the active substance in the aqueous suspension prepared and used according to the invention is present in a stable initial crystal form which does not change during processing so that changes in the crystal modification in solid pharmaceutical preparations of the difficultly soluble active substances prepared by the process according to the invention are substantially eliminated. This means that there are no significant conversion processes or uncontrolled recrystallisation to other crystal modifications during storage of the forms of administration. The adjuvants dissolved in the suspension are obtained in a partially or fully amorphous substance mixture after drying. This structure of the substance mixture is substantially maintained even in the case of storage for many years, and this has been confirmed, for example, by X-ray diffraction tests.

The subject matter of the present invention is also a fast-dissolving pharmaceutical preparation of a difficultly soluble active substance, preferably carvedilol, with a dissolution rate of at least 70% after 30 minutes, the active substance preferably being embedded in a partially or fully amorphous substance mixture or being enclosed in a partially or fully amorphous substance mixture.

The solid pharmaceutical preparations made according to the invention have a surprisingly high dissolution rate of at least 70%, preferably at least 80% after 30 minutes. More particularly, with the process according to the invention it is possible to prepare solid pharmaceutical preparations of carvedilol or 4-[2-hydroxy-3-[4-(phenoxymethyl)piperidino]-propoxy]-indole, acetate with this dissolution rate.

In comparison to this, the dissolution rates of the pure substances or powders of these active substances with hydrophilic adjuvants are in some cases far below 50% after 30 minutes. Due to the high tendency of these active substances to agglomerate, increasing the surface area by comminuting does not result in a significant improvement in the dissolution speed, even with the addition of hydrophilic adjuvants. Accordingly, the granulates, tablets and capsules prepared with the conventional methods and with conventional pharmaceutical adjuvants also have unsatisfactory active substance dissolution rates. Even if tablets are prepared with micronised active substance, the dissolution rate after 30 minutes is below 50% (cf. Examples 1 and 2).

The preparations made according to the invention can also be used as a basis for modified release preparations. Whereas, for example, in the case of conventional retard forms with difficultly soluble active substances the active substance release is determined not only by the retarding adjuvants but substantially also by the dissolution behavior of the difficultly soluble active substances, when the preparations according to the invention are used it is possible to achieve controlled release dependent solely on the retarding adjuvants.

The invention will be explained in detail hereinafter with reference to Examples.

EXAMPLE 1

Comparative Example

In-vitro dissolution rates of the active substances 4-[2-hydroxy-3-[4-(phenoxymethyl)piperidino]-propoxy]-indole (acetate form) (A) and carvedilol (B), or the comminuted forms with hydrophilic adjuvants—in powder form.

| Formulation | mg | Process | In-vitro dissolution rate after minutes in % | | | |
|---|---|---|---|---|---|---|
| | | | 10 | 20 | 30 | 60 |
| Active substance A | | Pure substance | 31 | 43 | 50 | 58 |
| Active substance A | 80 | Micronised | 40 | 46 | 53 | 62 |
| Lactose D 80 | 60 | together | | | | |
| Active substance B | | Pure substance | 36 | 46 | 49 | 56 |
| Active substance B | 30 | Micronised | 20 | 26 | 27 | 29 |
| Saccharose | 30 | together | | | | |
| Active substance B | 30 | Micronised | 24 | 26 | 27 | 29 |
| Lactose D 80 | 30 | together | | | | |

EXAMPLE 2

Comparative Example
Dissolution Rate of Tablets with Micronised Active Substance Jet comminuted carvedilol/lactose was mixed with other hydrophilic adjuvants and disintegrating agents such as lactose, poly(1-vinyl-2-pyrrolidone), cross-linked, and poly-(1-vinyl-2-pyrrolidone), granulated with a polyethylene stearate solution (Myrj 52), dried and screened. The granulate was mixed with conventional pharmaceutical adjuvants, such as poly(1-vinyl-2-pyrrolidone), cross-linked, highly dispersed silicon dioxide and magnesium stearate and pressed into tablets.

In-vitro dissolution rate of carvedilol after minutes in %:

| 10 | 20 | 30 | 60 | min |
|---|---|---|---|---|
| 22 | 36 | 42 | 50 | % |

The in-vitro dissolution rates in this and the following examples were determined in accordance with USP XXII, paddle method in an aqueous buffer pH 4.5

EXAMPLE 3

Carvedilol Suspension for Spray Drying.

75 mg Myrj 52 were dissolved in 700 g of water purified, and then 300 g carvedilol, 300 g saccharose and hydroxypropyl methyl cellulose was mixed into the solution with a high-speed stirrer. The aqueous suspension was spray dried.

In-vitro dissolution rate:

| 10 | 20 | 30 | 60 | min |
|---|---|---|---|---|
| 73 | 81 | 83 | 86 | % |

EXAMPLE 4

Carvedilol Tablets 69 g of the product spray-dried in accordance with Example 3 were mixed with hydrophilic adjuvants (e.g. lactose, saccharose, mannitol etc.), disintegrating agents (e.g. sodium carboxymethyl starch, poly(1-vinyl-2-pyrrolidone), cross-linked, corn starch), highly dispersed excipient (silicon dioxide, highly dispersed, aluminium oxide, etc.) and binder poly(1-vinyl-2-pyrrolidone) and granulated with water. The wet granulate was dried, screened and then pressed with a mould release agent (if required addition of a flow agent and/or disintegrating agent), to form tablets having an active substance content of 30 mg and a final weight of 180 mg.

In-vitro dissolution rate from the tablets:

| 10 | 20 | 30 | 60 | min |
|---|---|---|---|---|
| 81 | 88 | 96 | 98 | % |

EXAMPLE 5

Carvedilol Capsules

The product spray-dried in accordance with Example 3 was mixed with hydrophilic adjuvants, if required flow agents, disintegrating agents and mould release agents, and packed in capsules on conventional capsule filling machines.

In-vitro dissolution rate from the capsule filler:

| 10 | 20 | min |
|---|---|---|
| 95 | 100 | % |

EXAMPLE 6

Carvedilol Granulation Suspension 75 mg Myrj 52 were dissolved in 700 g water purified, and then 300 g carvedilol and 300 g saccharose were mixed into the solution with a high-speed stirrer.

EXAMPLE 7

Carvedilol Tablets

The aqueous granulation suspension according to Example 6 was absorbed on a mixture of hydrophilic adjuvants, disintegrating agent, highly dispersed excipient and binder, dried and screened.

Using a mould release agent, if required also a flow agent and disintegrating agent, tablets were made in an end weight of 180 mg with a content of 30 mg carvedilol.

In-vitro dissolution rate:

| 10 | 20 | 30 | 60 | min |
|----|----|----|----|-----|
| 78 | 90 | 93 | 97 | %   |

The active substance suspension according to the invention, or the spray products or granulates made therefrom, may contain a surfactant (e.g. polyoxyethylene stearate) in the form of Myrj 52 or Myrj 53. In the suspension, the ratio of active substance to surfactant can be in the range of up to 1:1, preferably up to 1:0.3.

If required, the adjuvant hydroxypropyl methyl cellulose (Pharmacaot 603) may be added in the spray drying suspension to improve the spraying and product properties.

EXAMPLE 8

4-[2-Hydroxy-3-[4-(phenoxymethyl)piperidino]-propoxy]-indole acetate

Suspension for Spray Drying

The active substance 4-[2-hydroxy-3-[4-(phenoxymethyl) piperidino]-propoxy]-indole acetate was stirred into an aqueous poly(1-vinyl-2-pyrrolidone) solution together with a highly dispersed excipient (e.g. highly dispersed silicon oxide) and a disintegrating agent (e.g. poly(1-vinyl-2-pyrrolidone), cross-linked, Primojel) and homogenised.

The aqueous suspension was spray dried.

In-vitro dissolution rate:

| 10 | 20 | 30 | 60  | min |
|----|----|----|-----|-----|
| 93 | 97 | 99 | 100 | %   |

EXAMPLE 9

4-[2-Hydroxy-3-[4-(phenoxymethyl)piperidino]-propoxy]-indole acetate

Granulation Suspension

The aqueous substance was stirred into an aqueous poly (1-vinyl-2-pyrrolidone) solution together with a highly dispersed excipient (e.g. highly dispersed silicon dioxide) and a disintegrating agent (e.g. poly(1-vinyl-2-pyrrolidone), cross-linked, Primojel) and homogenised.

The aqueous granulation suspension was absorbed on a mixture of hydrophilic adjuvants, disintegrating agents and highly dispersed excipient, dried and screened.

The application of the granulation suspension to the adjuvant mixture was carried out in a conventional mill, granulator or by spraying in a fluidised bed.

In-vitro dissolution rate of 4-[2-hydroxy-3-[4-(phenoxymethyl)piperidino]-propoxy]-indole acetate from granulate:

| 10 | 20 | 30 | 60 | min |
|----|----|----|----|-----|
| 71 | 88 | 94 | 97 | %   |

EXAMPLE 10

4-[2-Hydroxy-3-[4-(phenoxymethyl)piperidino]-propoxy]-indole acetate

Tablets and Capsules

Both the spray-dried suspension according to Example 8 and the granulate according to Example 9, obtained by absorbing the aqueous granulation suspension on special adjuvants, can be processed by methods known per se to form tablets, film tablets, dragees, pellets, hard gelatin capsules or soft gelatin capsules.

In-vitro dissolution rate of 4-[2-hydroxy-3-[4-(phenoxymethyl)piperidino]-propoxy]-indole acetate from tablets:

| 10 | 20 | 30 | 60 | min |
|----|----|----|----|-----|
| 84 | 92 | 94 | 96 | %   |

What is claimed is:

1. A process for preparing a pharmaceutical preparation comprising carvedilol or 4-[2-hydroxy-3-[4-(phenoxymethyl)piperidino]-propoxy]-indole and one or more water-soluble adjuvants, wherein the pharmaceutical preparation has a dissolution rate of at least 70% after 30 minutes, comprising (a) making an aqueous suspension from the carvedilol or 4-[2-hydroxy-3-[4-(phenoxymethyl) piperidino]-propoxy]-indole and one or more water-soluble adjuvants, and (b) spray drying the resulting aqueous suspension, with removal of water, to form a solid pharmaceutical preparation.

2. A process according to claim 1, wherein the active substance has a particle diameter of less than 500 μm.

3. A process according to claim 2, wherein the active substance has a particle diameter of less than 250 μm.

4. A process according to claim 3, wherein the active substance has a particle diameter of less than 100 μm.

5. A process according to claim 1, wherein the one or more water-soluble adjuvants are binders, fillers, disintegrating agents and/or surfactants.

6. A process according to claim 1, wherein the ratio of active substance to adjuvant in the dry substance in the suspension is 1:0.0 to 1:500.

7. A process according to claim 6, wherein the ratio of active substance to adjuvant in the dry substance in the suspension is 1:0.1 to 1:50.

8. A process according to claim 1, further comprising adding a surfactant to the aqueous suspension, wherein the ratio of active substance to surfactant is in the range of up to 1:1.

9. A process according to claim 8, wherein the ratio of active substance to surfactant is in the range of up to 1:0.3.

10. A process according to claim 8, further comprising dissolving a surfactant in water and then admixing the active substance together with one or more adjuvants.

11. A process according to claim 1, further comprising admixing a water-insoluble excipient in the aqueous suspension or applying he suspension to the excipient.

12. A process according to claim 11, further comprising stirring the active substance together with the water-insoluble excipient into an aqueous adjuvant solution, if required together with other water-soluble adjuvants.

13. A process according to claim 12, wherein the water-insoluble excipient is highly dispersed silicon dioxide or aluminum oxide.

14. A process according to claim 1, comprising making a solid pharmaceutical preparation by spray solidification from the active substance suspended in meltable adjuvants.

* * * * *